US009688667B2

(12) United States Patent
Thennati et al.

(10) Patent No.: US 9,688,667 B2
(45) Date of Patent: Jun. 27, 2017

(54) TAZAROTENE WITH LOW DIMER IMPURITY FOR TREATING ACNE OR PSORIASIS

(71) Applicant: SUN PHARMACEUTICAL INDUSTRIES LIMITED, Mumbai (IN)

(72) Inventors: Rajamannar Thennati, Baroda (IN); Rajeev Budhdev Rehani, Baroda (IN); Mukesh Nathalal Vaghela, Baroda (IN); Rashminkumar Rameshchandra Pandya, Baroda (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/103,444

(22) PCT Filed: Dec. 15, 2014

(86) PCT No.: PCT/IN2014/000776
§ 371 (c)(1),
(2) Date: Jun. 10, 2016

(87) PCT Pub. No.: WO2015/107542
PCT Pub. Date: Jul. 23, 2015

(65) Prior Publication Data
US 2016/0304503 A1    Oct. 20, 2016

(30) Foreign Application Priority Data
Dec. 13, 2013 (IN) ...................... 3909/MUM/2013

(51) Int. Cl.
| C07D 407/06 | (2006.01) |
| C07D 409/06 | (2006.01) |
| C07D 335/02 | (2006.01) |
| A61K 31/4436 | (2006.01) |

(52) U.S. Cl.
CPC ........ *C07D 409/06* (2013.01); *A61K 31/4436* (2013.01); *C07D 335/02* (2013.01)

(58) Field of Classification Search
None
See application file for complete search history.

(56) References Cited

FOREIGN PATENT DOCUMENTS

| WO | 2006/040644 A2 | 4/2006 |
| WO | 2009/116075 A2 | 9/2009 |
| WO | 2009116075 | * 9/2009 |

OTHER PUBLICATIONS

Brenna et al., Journal of Pharmaceutical and Biomedical Analysis 46 (2008) 574-576.*
International Search Report for PCT/IN2014/000776 dated Apr. 18, 2016.
Written Opinion for PCT/IN2014/000776 dated Apr. 18, 2016.

* cited by examiner

*Primary Examiner* — Karl J Puttlitz
(74) *Attorney, Agent, or Firm* — Sughrue Mion, PLLC

(57) ABSTRACT

The present invention relates to a method of treating acne or psoriasis by topically administering Tazarotene substantially free of dimer impurity of formula 4,4-dimethyl-6-[4-(4,4-dimethylthiochroman-6-yl)-buta-1,3-diynyl]-thiochroman.

8 Claims, 1 Drawing Sheet

%Change in ear thickness of female rats after topical application of Test items (A-F)- 0.1%Tazarotene solution in ethanol or Absolute ethanol, up to 14 days; dose 100 mcl/day on both the ears; n=6

%Change in ear thickness of female rats after topical application of Test items (A-F)- 0.1%Tazarotene solution in ethanol or Absolute ethanol, up to 14 days; dose 100 mcl/day on both the ears; n=6
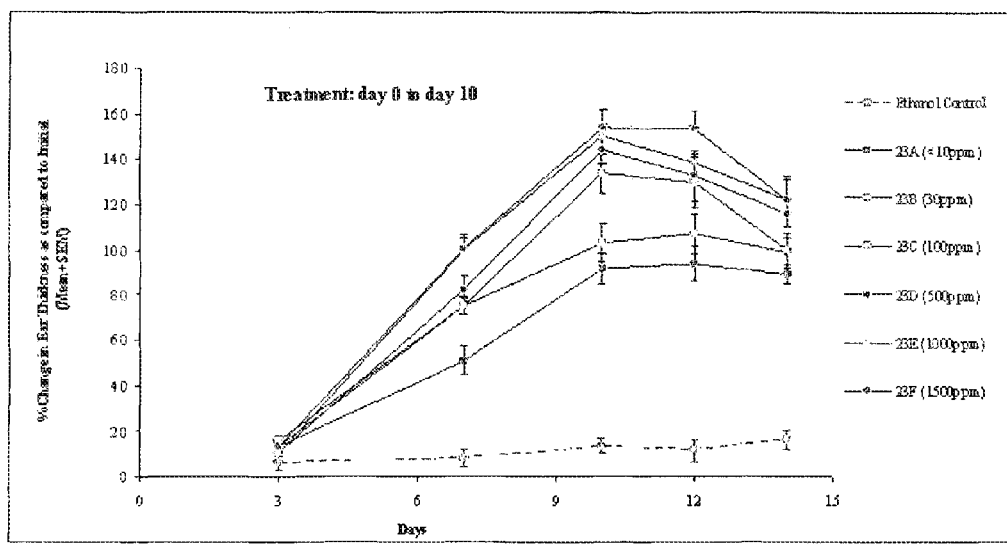

TAZAROTENE WITH LOW DIMER IMPURITY FOR TREATING ACNE OR PSORIASIS

FIELD OF INVENTION

The present invention relates to a method of treating acne or psoriasis by topically administering Tazarotene, a compound of formula (I), substantially free of dimer impurity 4,4-dimethyl-6-[4-(4,4-dimethylthiochroman-6-yl)-buta-1,3-diynyl]-thiochroman, a compound of formula (II)

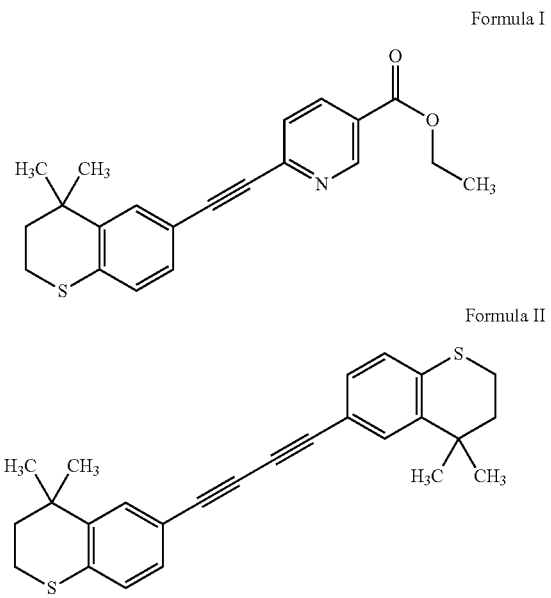

BACKGROUND OF THE INVENTION

Tazarotene (Formula I) is the international common accepted name for ethyl 6-[(4,4-dimethylthiochroman-6-yl) ethynyl]nicotinate, and has an empirical formula of $C_{21}H_{21}NO_2S$ and a molecular weight of 351.46. It is a synthetic retinoid used for the topical treatment of mild to moderate plaque psoriasis, acne vulgaris and photo aging.

U.S. Pat. No. 5,089,509 (the '509 patent) disclosed a process for preparation of tazarotene which includes following steps:

(a) reaction of 1-bromo-3-methyl-2-butene (formula III) with thiophenol (formula IV) to give phenyl 3-methylbut-2-enyl sulfide (formula V) followed by (b) cyclization of phenyl 3-methylbut-2-enyl sulfide with phosphorous pentoxide and phosphoric acid to yield 4,4-dimethylthiochroman (formula VI), (c) 4,4-dimethylthiochroman is then acetylated with acetyl chloride in the presence of stannic chloride to give 4,4-dimethyl-6-acetylthiochroman (formula VII), (d) 4,4-dimethyl-6-acetylthiochroman is reacted with lithium diisopropylamide and diethyl chlorophosphate to give 4,4-dimethyl-6-ethynylthiochroman (formula VIII), and (e) 4,4-dimethyl-6-ethynylthiochroman is reacted with ethyl 6-chloronicotinate (formula IX) in presence of butyl lithium, palladium tripehylphosphine and zinc chloride which resulted in formation of tazarotene (formula I). The reaction sequence is represented as per scheme-I:

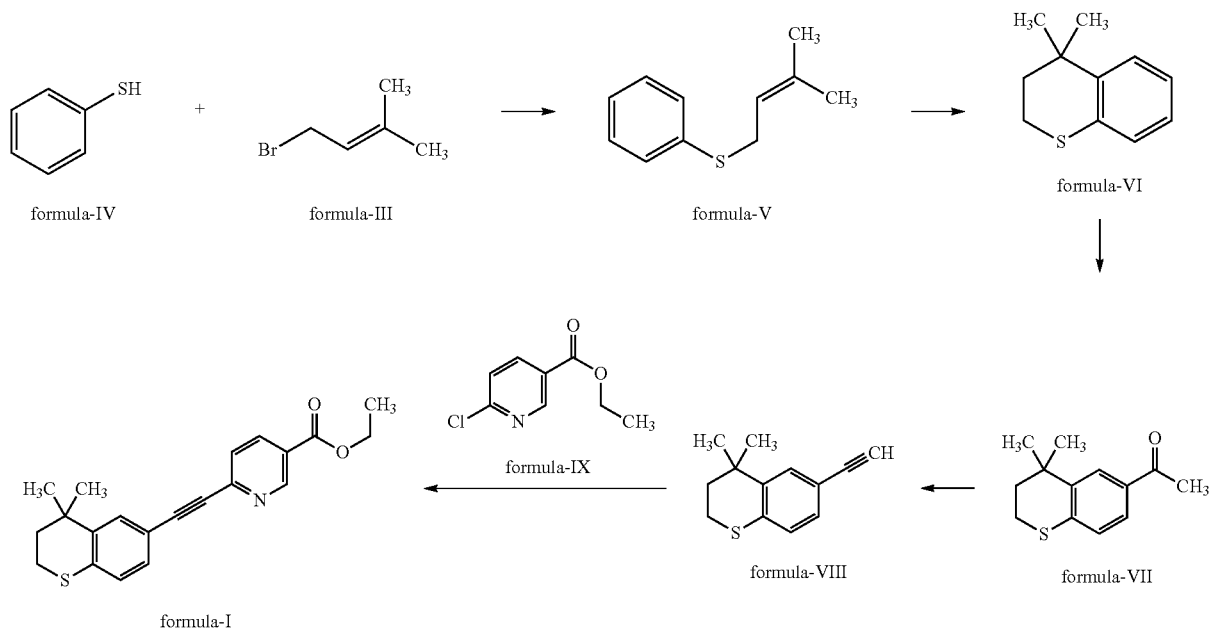

Scheme I

US Patent application No. 2006/0106233 discloses Sonogashira coupling of 4,4-dimethyl-6-ethynylthiochroman (formula VIII) with ethyl 6-chloronicotinate (formula IX) using triethnolamine, palladium catalyst and cuprous iodide to give tazarotene which is converted to its hydrochloride salt by treatment with ethyl acetate HCl solution.

PCT application No. 2006/040644 discloses use of sulfuric acid or p-toluenesulfonic acid for cyclization of phenyl 3-methylbut-2-enyl sulfide (formula V) to give 4,4-dimethylthiochroman (formula VI). It also discloses conversion of 4,4-dimethyl-6-acetylthiochroman (formula VII) to 4,4-dimethyl-6-ethynylthiochroman (formula VIII) by sequential reaction with hydrazine and iodine.

U.S. Pat. No. 5,602,130 (the '130 patent) discloses alternative method for preparation of 4,4-dimethyl-6-ethynylthiochroman (formula VIII) by using 4-bromothiophenol (formula X) instead of thiophenol. 4-Bromothiophenol is reacted with 1-bromo-3-methyl-2-butene (formula III) and subsequently cyclized to give 6-bromo-4,4-dimethylthiochroman (formula XII). 6-Bromo-4,4-dimethylthiochroman is coupled with trimethylsilylacetylene using palladium catalyst to give 6-(trimethylsilylethynyl)-4,4-dimethylthiochroman (formula XIII) which on desilylation with a base gives 4,4-dimethyl-6-ethynylthiochroman (formula VIII). The reaction sequence is represented as per scheme-II:

Scheme II

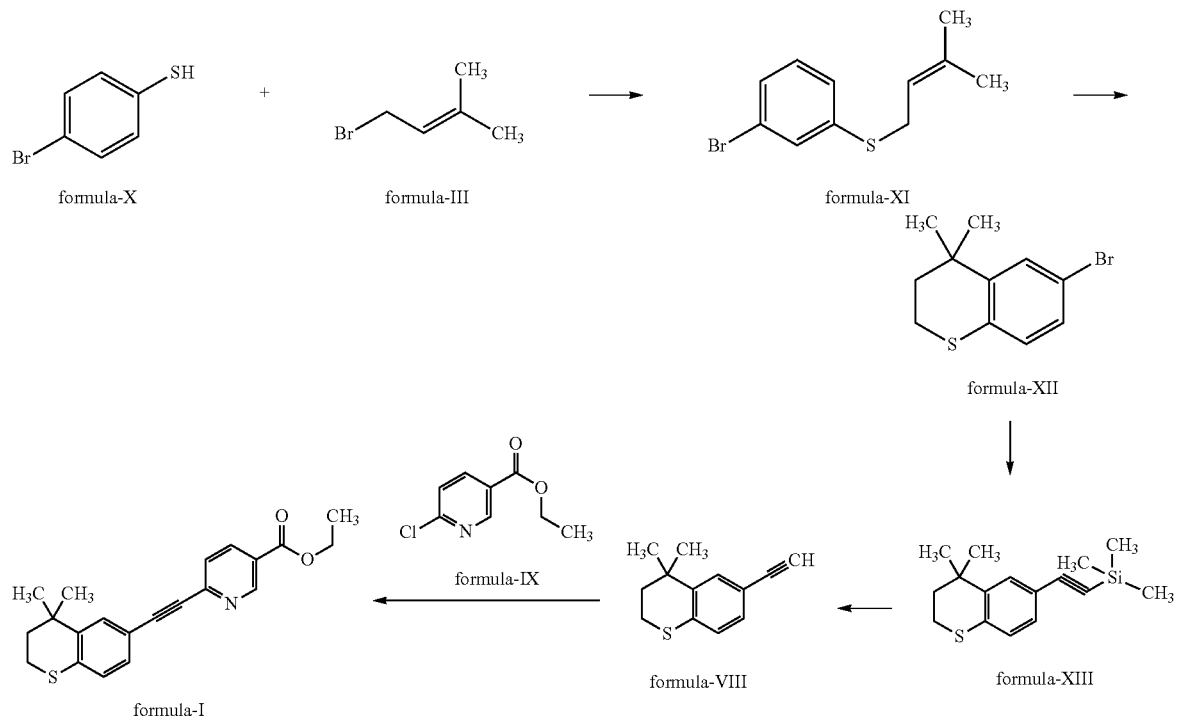

U.S. Pat. No. 7,273,937 discloses the process for preparation of tazarotene, wherein 4,4-dimethyl-6-bromothiochroman (formula XII) is oxidized to the corresponding 6-bromo-4,4-dimethylthiochroman-1-oxide (formula XIV), which is reacted with 2-methyl-3-butyn-2-ol to give 4-(4,4-dimethyl-1-oxothiochroman-6-yl)-2-methylbut-3-yn-2-ol (formula XV). The compound 4-(4,4-dimethyl-1-oxothiochroman-6-yl)-2-methylbut-3-yn-2-ol is deprotected to 4,4-dimethyl-6-ethynylthiochroman-S-oxide (formula XVI). 4,4-Dimethyl-6-ethynylthiochroman-S-oxide on reaction with ethyl 6-chloronicotinate (formula IX) in presence of catalyst palladium ligand results in compound of formula XVII, which on deoxygenation yields tazarotene (Formula I). The reaction sequence is represented as per Scheme-III:

Scheme III

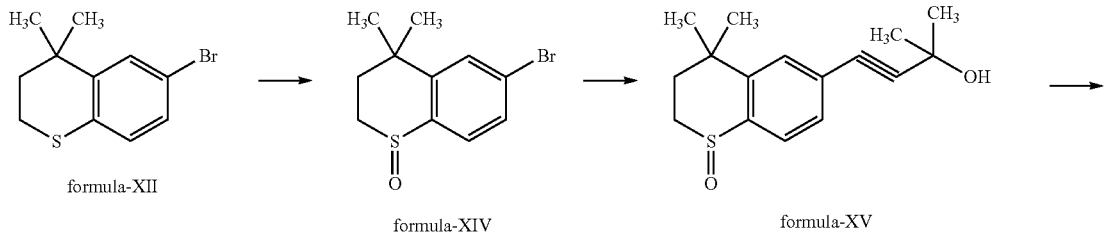

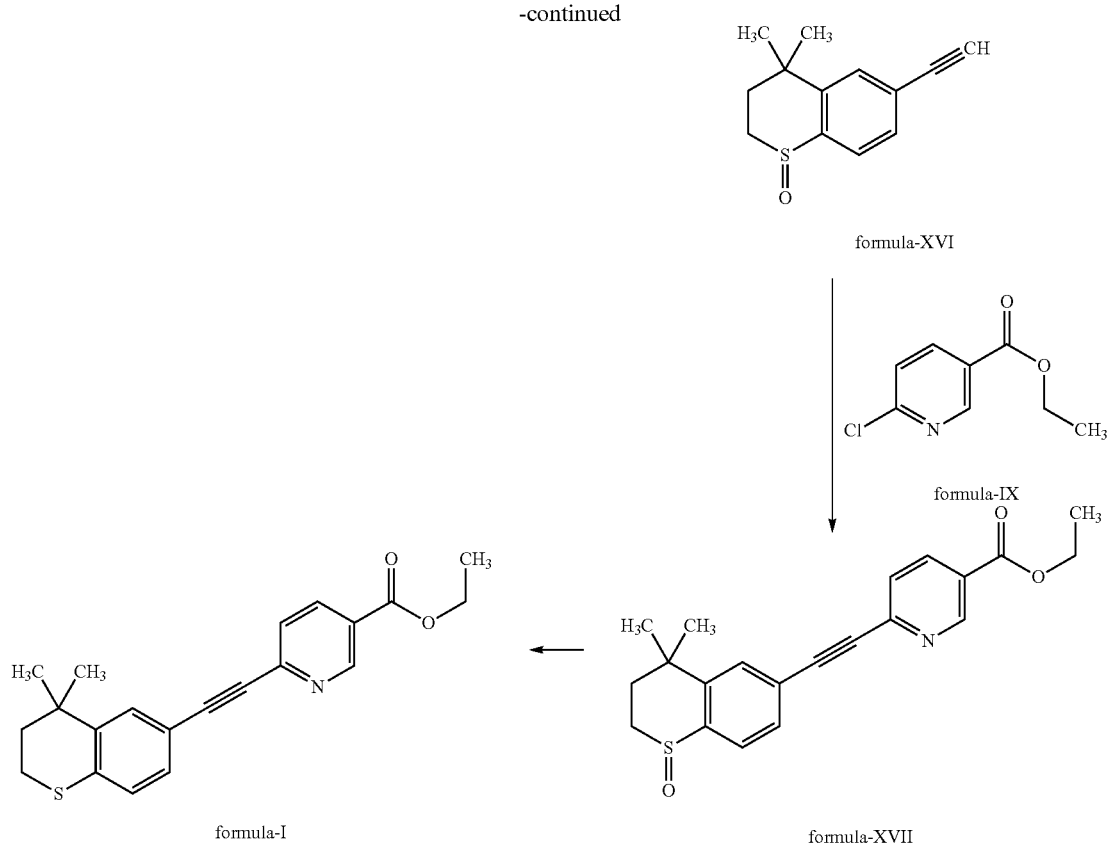
US Patent Application No. 2007/0238881 discloses preparation of tazarotene by coupling 6-chloronicotinonitrile (formula XVIII) with 4,4-dimethyl-6-ethynylthiochroman (formula VIII), subsequent hydrolysis and esterification as represented by Scheme IV.
Scheme IV
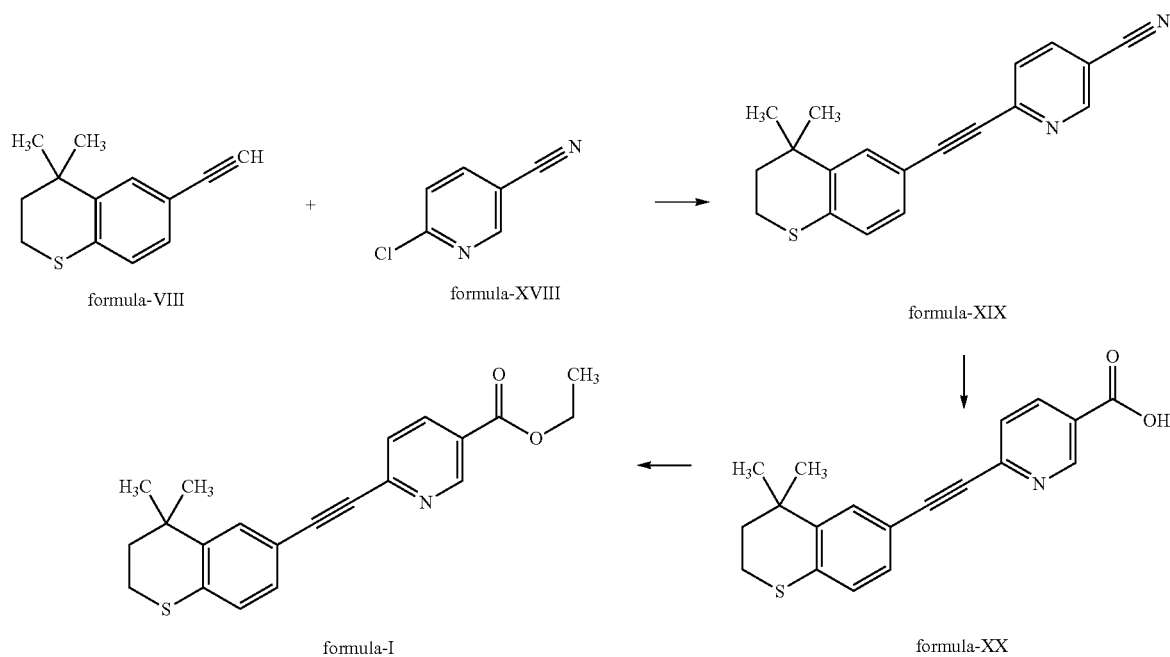

Tazarotene is available as cream, gel and aerosol foam in the markets.

Journal article titled "The safety and efficacy of tazarotene gel, a topical acetylenic retinoid, in the treatment of psoriasis" published in Archives of dermatology, Volume: 134, Issue: 1, Pages: 57-60 states that most common adverse effect associated with tazarotene were mild to moderate burning, pruritus, stinging and erythema. In most cases erythema was manifestation of mild to moderate irritation. Adverse events associated with tazarotene resulted in cessation of treatment in about 5% of patient population.

A dimer impurity 4,4-Dimethyl-6-[4-(4,4-dimethylthiochroman-6-yl)-buta-1,3-diynyl]-thiochroman, a compound of formula (II)

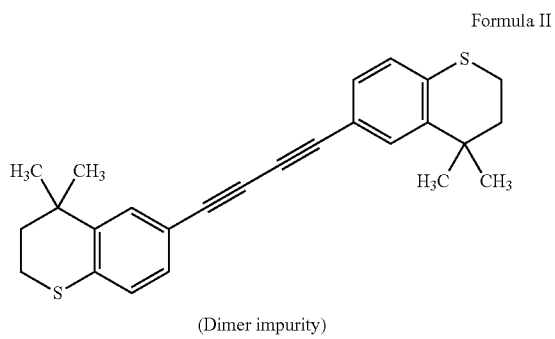 [SMILES: CC1(C)CCSc2ccc(C#CC#Cc3ccc4c(c3)C(C)(C)CCS4)cc21]

Formula II (Dimer impurity)

also referred as the dimer impurity in present specification may be formed due to homocoupling of 4,4-dimethyl-6-ethynylthiochroman used as an intermediate during the synthesis of tazarotene. Isolation and characterization of the dimer impurity is disclosed in Journal of Pharmaceutical and Biomedical Analysis, Volume: 46 (2008), Issue 3, Pages: 574-576, titled "Impurities of tazarotene: Isolation and structural characterization". However, the article is silent on the toxic properties of the impurity. In fact none of the literature available till date talks about the toxicity of this impurity. We have surprisingly found that this dimer impurity is is associated with side effects of tazarotene and treatment of acne or psoriasis using tazarotene substantially free of the impurity reduces the side effects.

BRIEF DESCRIPTION OF DRAWINGS

FIG. 1 shows the percent change in ear thickness of female rats after topical application of Test items (A-F)-0.1% Tazarotene solution in ethanol or Absolute ethanol, up to 14 days; dose 100 mcl/day on both the ears; n=6.

SUMMARY OF THE INVENTION

The present invention provides a method of treating acne or psoriasis by topically administering tazarotene, a compound of formula (I), substantially free of dimer impurity 4,4-dimethyl-6-[4-(4,4-dimethylthiochroman-6-yl)-buta-1,3-diynyl]-thiochroman, a compound of formula (II). In one aspect, the present invention provides a method of treating acne or psoriasis by topically administering tazarotene substantially free of dimer impurity of Formula II

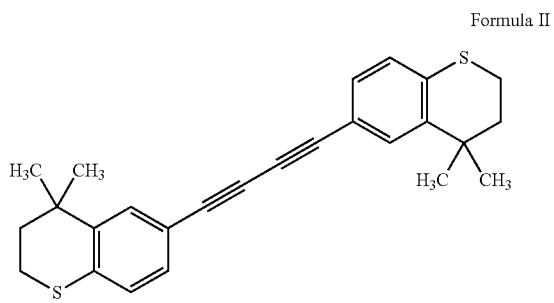 [SMILES: CC1(C)CCSc2ccc(C#CC#Cc3ccc4c(c3)C(C)(C)CCS4)cc21]

Formula II

In another aspect, the present invention provides a process for purification of a compound of Formula I (tazarotene) to obtain tazarotene having dimer impurity content of less than 100 ppm wherein the process comprises:
a. adding tazarotene containing dimer impurity of Formula II to an organic solvent,

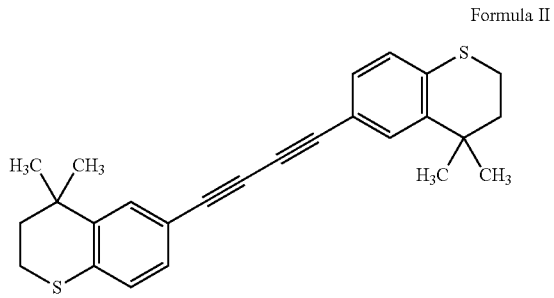 [SMILES: CC1(C)CCSc2ccc(C#CC#Cc3ccc4c(c3)C(C)(C)CCS4)cc21]

Formula II b. adding an acid and isolating the acid addition salt of tazarotene,
c. adding the tazarotene acid addition salt obtained in step b to an organic solvent and adding an aqueous solution of a base to obtain a biphasic mixture,
d. distilling the organic layer and treating the residue with a non-polar solvent,
e. optionally, repeating step a to d.

DESCRIPTION OF THE INVENTION

The present invention provides Tazarotene, a compound of formula (I), substantially free of dimer impurity 4,4-dimethyl-6-[4-(4,4-dimethylthiochroman-6-yl)-buta-1,3-diynyl]-thiochroman, a compound of formula (II). The term substantially free is intended to mean that the dimer impurity in tazarotene does not exceed 100 ppm when analyzed as per the analytical method exemplified in this specification.

The dimer impurity may be generated during Sonogashira coupling between 4,4-dimethyl-6-ethynylthiochroman and ethyl 6-chloronicotinoate, homocoupling of 4,4-dimethyl-6-ethynylthiochroman as shown in Scheme V.

Scheme V

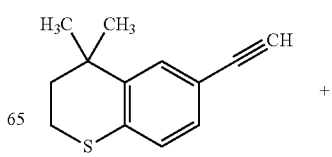

+

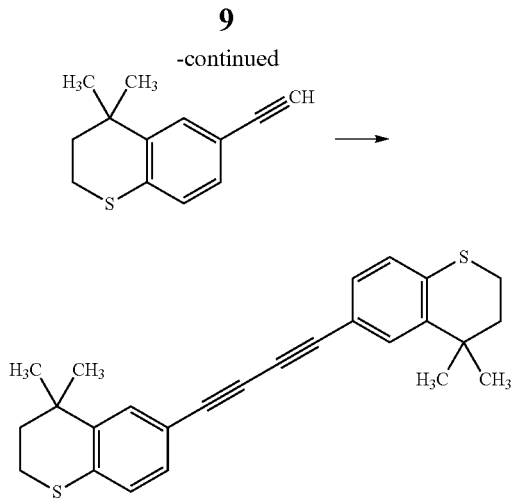

As provided in literature, the commercial tazarotene gel and creams possess many side effects like pruritus, burning/stinging, erythema, worsening of psoriasis, irritation, skin pain, rash, desquamation, irritant contact dermatitis, skin inflammation, fissuring, bleeding, and dry skin. There are reports of adverse effect in post marketing studies of these products too. The present inventors, during the animal studies, have found that the dimer impurity of Formula II is highly toxic and its content in the composition needs to be tightly controlled and restricted.

The inventors investigated the cause of death of 3 mice who had been exposed to tazarotene gel. It was found that the gel had a very high content of the order of 6000 ppm of the dimer impurity. This led to a detailed study on the toxicity of the dimer impurity.

Inventor performed the toxicity study of tazarotene spiked with known dimer impurity by applying the fixed concentration a solution of tazarotene (0.1% w/v tazarotene) with variable concentrations of impurity (0-1500 ppm) on Sprague Dawley Rats as given in Table 1.

TABLE 1

| Treatment Group | (0.1% w/v Tazarotene) | Impurity Level (ppm) | Volume of application/ear | Animal ID |
|---|---|---|---|---|
| 1 | Ethanol Control | 0 | 100 µl | 1-2 |
| 2 | 23A in ethanol | <10 | 100 µl | 3-4 |
| 3 | 23B in ethanol | 30 | 100 µl | 5-6 |
| 4 | 23C in ethanol | 100 | 100 µl | 7-8 |
| 5 | 23D in ethanol | 500 | 100 µl | 9-10 |
| 6 | 23E in ethanol | 1000 | 100 µl | 11-12 |
| 7 | 23F in ethanol | 1500 | 100 µl | 13-14 |

Table 1 shows the variable concentration of dimer impurity samples. Each sample (100 µl) was applied topically once daily on the left and right ear of the animals (Sprague Dawley Rats) of the respective groups from day 0 to day 9. Animals were checked for recovery from day 10 to day 14. Ear thickness measurement was repeated on day 3, 7, 10, 12 and 14. The results are provided in Table 2 and in FIG. 1.

TABLE 2

| Sample | Thickness (mm) | Day 3 | Day 7 | Day 10 | Day 12 | Day 14 |
|---|---|---|---|---|---|---|
| Ethanol Control | Mean | 0.50 | 0.51 | 0.53 | 0.52 | 0.54 |
|  | SEM | 0.010 | 0.013 | 0.017 | 0.016 | 0.013 |
|  | % | 6.3 | 8.4 | 13.6 | 11.7 | 16.4 |
| 23A (<10 ppm) | Mean | 0.53 | 0.71 | 0.89 | 0.90 | 0.88 |
|  | SEM | 0.020 | 0.031 | 0.027 | 0.035 | 0.022 |
|  | % | 13.6 | 51.1 | 91.6 | 93.6 | 88.9 |
| 23B (30 ppm) | Mean | $0.52^{ns}$ | $0.79^{ns}$ | $0.92^{ns}$ | $0.93^{ns}$ | $0.9^{ns}$ |
|  | SEM | 0.005 | 0.013 | 0.043 | 0.036 | 0.029 |
|  | % | 16.0 | 75.1 | 102.8 | 106.9 | 98.6 |
| 23C (100 ppm) | Mean | 0.52 | 0.81* | 1.07*** | 1.05*** | $0.92^{ns}$ |
|  | SEM | 0.007 | 0.026 | 0.028 | 0.031 | 0.028 |
|  | % | 13.5 | 75.3 | 133.3 | 129.7 | 100.0 |
| 23D (500 ppm) | Mean | 0.54 | 0.88*** | 1.16*** | 1.10*** | 1.02** |
|  | SEM | 0.014 | 0.032 | 0.013 | 0.038 | 0.017 |
|  | % | 11.0 | 82.5 | 143.9 | 132.6 | 115.5 |
| 23E (1000 ppm) | Mean | 0.51 | 0.93*** | 1.16*** | 1.11*** | 1.03*** |
|  | SEM | 0.12 | 0.042 | 0.015 | 0.0123 | 0.049 |
|  | % | 10.1 | 99.8 | 150.2 | 138.5 | 122.0 |
| 23F (1500 ppm) | Mean | 0.52 | 0.92*** | 1.17*** | 1.17*** | 1.02*** |
|  | SEM | 0.006 | 0.011 | 0.024 | 0.029 | 0.046 |
|  | % | 13.5 | 100.3 | 153.6 | 153.1 | 121.9 |

The ear thickness (mm) data were analyzed using Two-way ANOVA followed by Bonferroni post tests (n = 6). Differences were considered to be statistically significant when
$^{ns}$Non significant,
*** = $p < 0.001$ as compared to Test item 1(23A, impurity levels <10 ppm).

Inventors found that the level of dimer impurity in tazarotene samples upon topical application cause dose dependent and significant increase in the ear thickness and inflammation. Complete recovery was observed in Test item 23B (30 ppm impurity) and Test item 23C (100 ppm) whereas no complete recovery was observed in Test item 23D (500 ppm), Test item 23E (1000 ppm) and Test item 23F (1500 ppm) as compared to Test item 23A (impurity <10 ppm). Hence, in order to reduce the adverse effect of tazarotene the content of the dimer impurity should be controlled to minimum level.

In one aspect, the present invention provides a method of treating acne or psoriasis by topically administering tazarotene substantially free of dimer impurity of Formula II.

In an embodiment the content of dimer impurity in tazarotene is less than 100 ppm. Preferably, the content of the dimer impurity is less than 30 ppm. More preferably, the content of the dimer impurity is less than 10 ppm. Most preferably, the content of the dimer impurity is less than 5 ppm.

The method of the present invention requires application of a topical composition of tazarotene wherein, the content of a compound of Formula II in tazarotene is less than 50 ppm. Preferably, the content of the dimer impurity is less than 30 ppm. More preferably, the content of the dimer impurity is less than 10 ppm. Most preferably, the content of the dimer impurity is less than 5 ppm.

The term a "topically administrable composition," or "topical composition," or a "topical formulation," as used herein, means any formulation or composition which is pharmaceutically acceptable for topical delivery of the specified compound according to embodiments of the invention. Exemplary forms of composition that can be used for topical administration in embodiments, of the present invention include, but are not limited to, sprays, mists, aerosols, solutions, lotions, gels, creams, ointments, pastes, unguents, emulsions and suspensions.

In another aspect, the present invention provides a process for preparation of Tazarotene substantially free of dimer impurity of Formula II comprising:
  a. adding Tazarotene containing dimer impurity of Formula II to an organic solvent,
  b. adding an acid and isolating the acid addition salt of tazarotene,
  c. adding the tazarotene acid addition salt obtained in step b to an organic solvent and adding an aqueous solution of a base to obtain a biphasic mixture,
  d. distilling the organic layer and treating the residue with a non-polar solvent,
  e. optionally, repeating step a to d.

Tazarotene used in step 'a' with high dimer impurity content of 400 ppm or more can be obtained by the processes known in the art for example the '509 patent. Tazarotene containing dimer impurity is dissolved in an organic solvent selected from the group comprising of ester like ethyl acetate, ethyl butyrate, isopropyl acetate, methyl acetate, methyl propionate, propyl acetate etc., ether like dioxane, tetrahydrofuran (THF), 2-methyl tetrahydrofuran, diethyl ether, methyl tert-butyl ether, diisopropyl ether etc., saturated hydrocarbon like hexane, heptane etc., aromatic hydrocarbon like toluene, benzene etc., halogenated solvent like carbon tetrachloride, chlorobenzene, chloroform, 1,1-dichloroethane, 1,2-dichloroethane, dichloromethane etc., or mixtures thereof. In step 'b' Tazarotene with dimer impurity content of more than 400 ppm is converted into its acid addition salt via reaction with suitable acid in a manner well known to those skilled in the art. A solution of inorganic mineral acid is added to above solution to get precipitate of tazarotene acid addition salt. Solution of inorganic mineral acid can be made in a compatible solvent like water or an alcohol. Alcohol used in the step can selected from the group of C1-C4 alkanols. Preferably, the alcohol is ethanol. Inorganic mineral acid used in the step can be selected from the group of hydrochloric acid, sulfuric acid, nitric acid, phosphoric acid. Preferably, the inorganic mineral acid is hydrochloric acid. The precipitate is filtered, washed with the organic solvent and dried to give tazarotene acid addition salt. The organic solvent used for washing can be same as that used for salt preparation. As an embodiment of step 'c' the tazarotene acid addition salt is suspended in a water immiscible organic solvent selected from the group of ether like dioxane, tetrahydrofuran (THF), 2-methyl tetrahydrofuran, diethyl ether, methyl tert-butyl ether, diisopropyl ether etc., $C_6$ to $C_7$ substituted or unsubstituted acyclic or cyclic aliphatic hydrocarbon like hexane, heptane, cyclohexane etc., aromatic hydrocarbons like toluene, benzene etc., and treated with an aqueous solution of inorganic base. The inorganic base is selected from the group of sodium carbonate, sodium bicarbonate, potassium carbonate, potassium bicarbonate, lithium carbonate, lithium bicarbonate, cesium carbonate, cesium bicarbonate. Organic layer is separated, dried and concentrated to get tazarotene free base. As an embodiment of step 'd', tazarotene obtained in step 'c' is suspended in non-polar organic solvent and stirred for 30 minutes to 3 hours. The mixture can be heated to temperature from 40° C. to reflux temperature of the solvent. The non-polar solvent is selected from the group of n-heptane, hexane, cyclohexane, benzene, toluene, cyclopentane, pentane, 1,4-dioxane, diethyl ether. The suspension is filtered and dried to obtain tazarotene with content of dimer impurity of less than 100 ppm.

If required, step a to step d may be repeated 1 to 3 times to obtain the desired purity of tazarotene.

In another embodiment of the invention, tazarotene obtained by the process can be formulated into topical compositions like cream, gel or aerosol foam.

The examples that follow do not limit the scope of the present invention and are included as illustrations.

Example 1: Preparation of Crude Tazarotene

To 188 ml of toluene was added palladium on carbon (10 g) under $N_2$ atmosphere. The mixture was heated to 105-115° C. to remove water by azeotropic distillation. The reaction mass was cooled to 50-55° C. To the above mixture, anhydrous sodium sulphate (12.5 g), anhydrous potassium carbonate (37.5 g), triphenylphosphine (5 g), ethyl 6-chloronicotinoate (12.5 g) and toluene (12.5 ml) were added at 50-55° C. and stirred for 2 hours. To the above mixture, 4,4-dimethyl-6-ethynylthiochroman (10 g), cuprous iodide (0.06 g) and toluene (12.5 ml) were added and the reaction mixture was heated to 105-115° C. for 10-12 hours. The reaction mixture was cooled to 25-30° C. and water (125 ml) was' added. The biphasic reaction mixture was filtered and from the filtrate, product enriched organic layer was separated. The organic layer was washed with water (2×65, ml) and brine solution (2×65 ml), dried over anhydrous sodium sulphate (5 g) and all the solvent was distilled off to get residual mass. The residual mass was dissolved in n-heptane (50 ml) at 75-80° C., which was treated with activated charcoal, neutral alumina and filtered. The filtrate was stirred at 25-30° C. for 20 hours. The resulted solid was filtered off, washed with n-heptane (12.5 ml) and dried to yield 9 g of tazarotene. (HPLC purity of tazarotene—97.64%; Content of dimer impurity—1.31%).

Example 2: Preparation of Tazarotene Hydrochloride

Tazarotene (9 g, obtained in example 1) was suspended in ethyl acetate (135 ml) at 25-30° C. To the above suspension ethanolic HCl (15 ml) was added and stirred for 2 hours. The resulted solid was filtered and washed with ethyl acetate (75 ml) and dried to yield 10 g of tazarotene hydrochloride. (HPLC purity of tazarotene hydrochloride—99.28%, Content of dimer impurity—0.01%)

Example 3: Preparation of Pure Tazarotene

Tazarotene hydrochloride (10 g as obtained in example 2) was suspended in ethyl acetate (100 ml) at 25-30° C. To the above suspension saturated aqueous sodium bicarbonate solution was added to get biphasic mixture. The product enriched organic layer was separated, washed with brine solution, dried over anhydrous sodium sulfate (5 g) and solvent was distilled off completely to get residual mass. To the residual mass n-heptane (50 ml) was added and stirred at 25-30° C. for 1 hour. The resulting solid was filtered off, washed with n-heptane and dried to obtain 9 g of pure tazarotene. (HPLC purity of tazarotene—99.8%, Content of dimer impurity—Nil)

Example 4: Determination Dimer Impurity of Tazarotene

Buffer Preparation:
Potassium dihydrogen orthophosphate (3.4 g) was dissolved in 1000 ml water and pH of the solution was adjusted to 7.00±0.05 with triethylamine.
Mobile Phase:
Mobile phase prepared by mixing 100 volumes of buffer solution, 900 volumes of methanol.
Diluent:
Acetonitrile.
Standard Stock Preparation:
About 1.0 mg of dimer impurity Reference Standard (RS) was transferred into 100 ml volumetric flask and dissolved with 5 ml tetrahydrofuran and diluted up to mark with diluent.
Standard Preparation:
Standard stock solution (1 ml) was transferred to 20 ml volumetric flask and diluted up to mark with diluent.
Sample Preparation:
About 50 mg accurately weighed sample was transferred into a 5 ml volumetric flask. Tetrahydrofuran (1 ml) was added to dissolve and then diluted up to mark with diluent.
Blank Preparation:
About 1 ml tetrahydrofuran was transferred into a 5 ml volumetric flask and diluted up to mark with diluent.
Instrumental Conditions:
Ultra-Performance Liquid Chromatograph (UPLC) with the following conditions.
Column: Acquity UPLC BEH C18, (50×2.1) mm, 1.7μ
Detector: 215 nm UV detector
Injection volume: 2 μl
Column oven Temp.: 50° C.
Flow rate: 0.3 ml/min
Sample cooler: 10° C.
Run time: 5 minute
Sampling rate: 20 pts/sec
Procedure:
Blank (2 μl) followed by six replicates of standard preparation were injected into the chromatograph set to above conditions and chromatograms were recorded.
Retention time of dimer impurity is about 2.6 min. Percentage RSD of area counts for dimer Impurity peak was calculated from standard preparation.
The system is valid only if the % RSD of area counts for dimer Impurity peak is not more than 10.0%.
Sample preparation (2 μl) was injected into the system and content of dimer impurity was calculated the using the following formula:

$$\text{Dimer Impurity (ppm)} = \frac{AT}{AS} \times \frac{WS}{100} \times \frac{1}{20} \times \frac{5}{WT} \times P \times 10000$$

where,
AT=Area of dimer impurity in sample preparation.
AS=Mean area of dimer impurity in standard preparation.
WS=Weight of dimer impurity RS in standard preparation (in mg.)
WT=Weight of sample in mg.
P=% Potency of dimer impurity RS (as is basis).

Table for LOD-LOQ:

| Component name | Limit of Detection (LOD) | Limit of Quantification (LOQ) |
|---|---|---|
| Dimer Impurity 6-[4-(4,4-Dimethylthio chroman-6-yl) buta-1,3-diynyl]-4,4-dimethyl-thiochroman | 0.72 ppm | 5.99 ppm |

Example 5: Composition for Tazarotene Gel (0.1% w/w)

| Ingredients | Concentration (% w/w) |
|---|---|
| Disodium Edetate | 0.05 |
| Ascorbic acid | 0.1 |
| Carbomer homopolymer type B | 1.25 |
| Poloxamer 407 | 0.2 |
| Tazarotene | 0.1 |
| Polyethylene Glycol 400 | 45 |
| Hexylene Glycol | 2 |
| Butylated hydroxy toluene | 0.05 |
| Butylated hydroxy anisole | 0.1 |
| Polysorbate 40 | 0.2 |
| Benzyl alcohol | 1 |
| Tromethamine | 0.8 |
| Purified water | q.s. |

The invention claimed is:

1. A method of treating acne or psoriasis by topically administering tazarotene comprising less than 100 ppm of a dimer impurity of Formula II

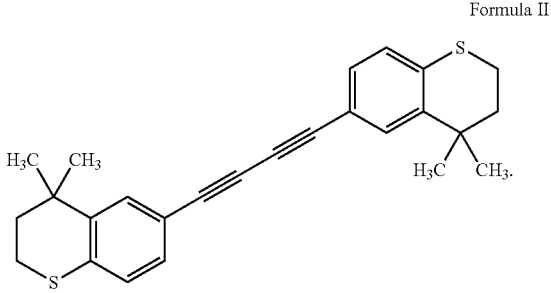 [SMILES: CC1(C)CCSc2ccc(C#CC#Cc3ccc4c(c3)C(C)(C)CCS4)cc21]

Formula II

2. The method of claim 1 wherein, the tazarotene contains less than 30 ppm of dimer impurity of Formula II.

3. The method of claim 1 wherein, the tazarotene contains less than 10 ppm of dimer impurity of Formula II.

4. The method of claim 1 wherein, the dimer impurity of Formula II in tazarotene is not detectable in said tazarotene.

5. A process for preparation of tazarotene comprising less than 100 ppm of a dimer impurity of Formula II

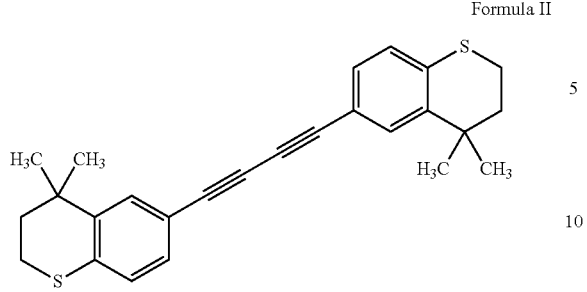

Formula II comprising:
a. adding tazarotene containing dimer impurity of Formula II to an organic solvent,
b. adding an acid and isolating the acid addition salt of tazarotene,
c. adding the tazarotene acid addition salt obtained in step b to an organic solvent and adding an aqueous solution of a base to obtain a biphasic mixture,
d. distilling the organic layer and treating the residue with a non-polar solvent,
e. optionally, repeating step a to d.

6. Tazarotene, obtained by the process of claim 5 containing less than 30 ppm of dimer impurity of Formula II.

7. Tazarotene, obtained by the process of claim 5 containing less than 10 ppm of dimer impurity of Formula II.

8. Tazarotene, obtained by the process of claim 5 wherein dimer impurity of Formula II is not detectable in said Tazarotene.

* * * * *